US006719982B1

(12) United States Patent
Coffin et al.

(10) Patent No.: US 6,719,982 B1
(45) Date of Patent: Apr. 13, 2004

(54) MUTANT HERPES SIMPLEX VIRUSES AND USES THEREOF

(75) Inventors: Robert S. Coffin, London (GB); David S. Latchman, London (GB); Nicholas J. Finnie, Winchester (GB)

(73) Assignee: Biovex Limited, London (GB)

( * ) Notice: Subject to any disclaimer, the term of this patent is extended or adjusted under 35 U.S.C. 154(b) by 0 days.

(21) Appl. No.: 09/601,102

(22) PCT Filed: Jan. 29, 1999

(86) PCT No.: PCT/GB99/00306

§ 371 (c)(1),
(2), (4) Date: Feb. 20, 2001

(87) PCT Pub. No.: WO99/38955

PCT Pub. Date: Aug. 5, 1999

(30) Foreign Application Priority Data

Jan. 29, 1998 (GB) ............................................. 9801930

(51) Int. Cl.[7] ...................... A61K 39/245; A61K 39/12; A61K 39/295; C12N 7/01; C12N 15/00
(52) U.S. Cl. ............................... 424/231.1; 424/199.1; 424/202.1; 435/235.1; 435/320.1
(58) Field of Search .................. 514/44; 424/199.1, 424/202.1, 231.1; 435/5, 235.1, 236, 320.1

(56) References Cited

U.S. PATENT DOCUMENTS

| | | | |
|---|---|---|---|
| 5,658,724 A | | 8/1997 | DeLuca |
| 5,665,362 A | * | 9/1997 | Inglis et al. ............. 424/205.1 |
| 6,010,908 A | * | 1/2000 | Gruernert et al. ........... 435/463 |

FOREIGN PATENT DOCUMENTS

| | | |
|---|---|---|
| WO | WO 97/10349 | 3/1997 |
| WO | 98 04726 A | 2/1998 |
| WO | WO 98/30707 | 7/1998 |

OTHER PUBLICATIONS

Lilley et al. Journal of Virology. 2001; 75 (9): 4343–4356.*
Verma et al. Nature. 1997; 389: 239–242*
Wildner. Annals of Medicine. 1999; 31 (6): 421–9, abstract only.*
Grignet–Debrus et al. Cancer Gene Therapy. 2000; 7 (2): 215–23, abstract only.*
Rouse et al. Journal of Virology. 1994; 68 (9): 5685–9, abstract only.*
Jones et al. Journal of Virology. 1995; 69 (8): 4863–4871.*
Chou et al. Science. 1990; 250: 1262–1266.*
Dobson et al. (Neuron. 1990; 5: 353–360.*
Ace et al. Journal of Virology. 1989; 63 (5): 2260–9.*
Howard M K et al: :Gene delivery to rat enteric neurons using herpes simpex virus–based vectors. Journal of molecular neuroscience, (Oct. 1997) 9 (2) 65–74.

Coffin et al, "Herpes Simplex Virus–Based Vectors", Chapter 6, Genetic Manipulation of the Nervous System, pp. 99–114 (1996).

MacLean et al, "Herpes simplex virus type 1 deletion variants 1714 and 1716 pinpoint neurovirulence–related sequences in Glasgow strain 17[+] between immediate early gene 1 an the 'a' sequence", Journal of General Virology 72:631–639 (1991).

Shinnick et al, "Nucleotide sequence of Moloney murine leukaemia virus", Nature 293:543–548 (1981).

Morgenstern and Land, "A series of mammalian expression vectors and characterisation of their expression of a reporter gene in stably and transiently transfected cells", Nucleic Acids Research 18(4):1068 (1990).

Ace et al. "Construction and Characterization of a Herpes Simplex Virus Type 1 Mutant Unable To Transinduce Immediate–Early Gene Expression", Journal of Virology 63(5):2260–2269 (1989).

McFarlane et al. "Hexamethylene bisacetamide stimulates herpes simplex virus immediate early gene expression in the absence of trans–induction by Vmw65", Journal of General Virology 73:285–292 (1992).

Hardy et al, "Herpes Simplex Virus Inhibits Host Cell Splicing, and Regulatory Protein ICP27 Is Required for This Effect", Journal of Virology 68(12):7790–7799 (1994).

Dobson et al, "A Latent Nonpathogenic HSV–1 Derived Vector Stably Expresses—Galactosidase in Mouse Neurons", Neuron 5:353–360 (1990).

Chou et al, "Mapping of Herpes Simplex Virus–1 Neurovirulence to $\gamma_1 34.5$, a Gene Nonessential for Growth in Culture", Science 250:1262–1266 (1990).

Chiocca et al, "Transfer and Expression of the IacZ Gene in Rat Brain Neurons Mediated by Herpes Simplex Virus Mutants", The New Biologist 2(8):739–746 (1990).

Chou and Roizman, "The $\gamma_1 34.5$ gene of herpes simplex virus 1 precludes neuroblastoma cells from triggering total shutoff of protein synthesis characteristic of programmed cell death in neuronal cells"Proc. Natl. Acad. Sci. USA 89:3266–3270 (1992).

Chou et al, "Differential Response of Human Cells to Deletions and Stop Codons in the $\gamma_1 34.5$ Gene of Herpes Simplex Virus", Journal of Virology 68(12):8304–8311 (1994).

(List continued on next page.)

Primary Examiner—James Housel
Assistant Examiner—Shanon Foley
(74) Attorney, Agent, or Firm—Nixon & Vanderhye P.C.

(57) ABSTRACT

The present invention provides a herpes simplex virus strain having a functional ICP27 gene and lacking at lease a functional ICP4 gene and a functional ICP34.5 gene. It also provides the use of a herpes simplex virus strain which lacks at least a functional ICP4 gene and a functional ICP34.5 gene in the treatment of disorders of, or injuries to, the nervous system of a mammal.

15 Claims, No Drawings

OTHER PUBLICATIONS

DeLuca et al, "Isolation and Characterization of Deletion Mutants of Herpes Simplex Virus Type 1 in the Gene Encoding Immediate–Early Regulatory Protein ICP4", Journal of Virology 56(2):558–570 (1985).

Lokensgard et al. "Long–Term Promoter Activity during Herpes Simplex Virus Latency", Journal of Virology 68(11):7148–7158 (1994).

Saffrey et al, "Growth of enteric neurones from isolated myenteric ganglia in dissociated cell culture", Cell Tissue Res. 265:527–534 (1991).

Smiley and Duncan, "Truncation of the C–Terminal Acidic Transcriptional Activation Domain of Herpes Simplex Virus VP16 Produces a Phenotype Similar to That of the in1814 Linker Insertion Mutation", Journal of Viruloty 71(8):6191–6193 (1997).

Howard and Duncan, "High efficiency gene transfer to the central nervous system of rodents and primates using herpes virus vectors lacking functional ICP27 and ICP34.5", Gene Therapy 5:1137–1147 (1998).

Samaniego et al, "Persistence and Expression of the Herpes Simplex Virus Genome in the Absence of Immediate Early Proteins", Journal of Virology 72(4):3307–3320 (1998).

Dilloo et al. "A novel herpes vector for the high–efficiency transduction of normal and malignant human hematopoietic cells" Blood 89:119–127 (1997).

Goins et al. "Herpes simplex virus type 1 vector–mediated expression of nerve growth factor protects dorsal root ganglion neurons from peroxide toxicity" J. Virol. 73:519–532 (1999).

Palella et al. "Herpes simplex virus–mediated human hypoxanthine–guanine phosphoribosyltransferase gene transfer into neuronal cells" Mol. Cell. Biol. 8:457–460 (1988).

* cited by examiner

MUTANT HERPES SIMPLEX VIRUSES AND USES THEREOF

FIELD OF THE INVENTION

The present invention relates to mutant herpes simplex viruses which have inactivating mutations rendering them non-pathogenic. It also relates to the use of such mutant herpes simplex viruses in gene therapy and in methods of assaying for gene function.

BACKGROUND TO THE INVENTION

Herpes simplex virus (HSV) has often been suggested as a suitable vector for the nervous system due to its neurotrophic lifestyle and its ability to remain in neurons for the lifetime of the cell. However wild type HSV is highly pathogenic and must, like most viral vectors, be disabled in some way. The pathogenic effects of HSV result from lytic infection with the virus and therefore the use of HSV as a vector requires the development of strains carrying mutations that disrupt the lytic cycle whilst allowing the establishment of asymptomatic latent infections.

HSV vectors have previously been produced and tested in vivo by the deletion of the essential immediate early (IE) gene ICP4 (Dobson et al., 1990 and Chiocca et al., 1990), which must be complemented for growth in culture. ICP4 is required for transcriptional activation of the viral early and late genes in lytic infection. Thus, a virus lacking this gene can readily infect cells but cannot grow lytically. Another essential gene is ICP27, whose gene product is highly cytotoxic probably due to its secondary role of preventing the splicing of pre-mRNAs in favour of translation from the mainly unspliced herpes RNAs. HSV strains have been produced with deletions in ICP27, either in ICP27 alone (for example Reef Hardy and Sandri-Goldin, 1994 and Rice and Knipe, 1990), or in combination with ICP4 (for example U.S. Pat. No. 5,658, 724).

Mutations have also been made in non-essential genes such as the IE gene ICP0, the IE gene ICP6, tyrosine kinase (TK), US5 or VMW65, all of which are required for full pathogenicity in vivo but are dispensable for growth in culture (reviewed by Coffin and Latchman, 1996). These types of mutation provide the added advantage that the deletion need not be complemented for growth in culture, which has been shown previously to occasionally result in reversion of the non-pathogenic phenotype to a wild-type phenotype by homologous recombination between the virus and the complementing sequences in the cell-line during growth. However in each of these cases, mutation of the non-essential gene does not completely prevent virus replication since high titre inoculation will overcome the block to replication in vivo.

ICP34.5, the so-called neurovirulence factor, is absolutely required for neurovirulence in vivo, but is unnecessary for growth in culture (Chou et al., 1990). Mutations in ICP34.5 provide a subtle mechanism by which HSV can be disabled. ICP34.5 is thought to prevent the usual host response to a productive infection in neurons, which results (in the absence of ICP34.5) in cell death and thus the limitation of the infection to initially infected cells. ICP34.5 is thought to override this response and allow full lytic replication to occur. Thus in the absence of ICP34.5, if a disabled virus were ever to re-establish a productive infection for whatever reason, the ICP34.5 mutation would ensure that the protective host response limited virus replication to a small number of cells.

It is, however, unlikely that viruses carrying a single defect will be considered safe enough for eventual human use. Added safety and the possibility of higher titre inoculation might be achieved by the inactivation of an essential IE gene providing an absolute block to replication (and which must thus be complemented in culture), together with inactivation of a non-essential gene.

SUMMARY OF THE INVENTION

We have now found that herpes simplex viruses carrying inactivating mutations in at least ICP4 and ICP34.5 (optionally with inactivating mutations in VMW65 and/or vhs) exhibit reduced levels of toxicity compared to virus strains carrying mutations in ICP34.5 alone, ICP34.5 together with VMW65, or ICP34.5 together with VMW65 and vhs. They are safer than viruses deleted for ICP4 alone. These highly mutated strains can however still be grown efficiently in culture, using an ICP4 complementing cell line, allowing preparation of stocks of the virus. Furthermore, these HSV strains of the invention have been shown to be suitable vectors for delivery of heterologous genes to mammalian cells.

Thus the present invention provides a herpes simplex virus (HSV) having a functional ICP27 gene and which lacks at least a functional ICP4 gene and a functional ICP34.5 gene. Preferably said virus further lacks one or more functional non-essential genes other than the said ICP34.5 gene. For example the virus may further lack one or more functional non-essential genes selected from VMW65, vhs, ICP0, ICP6 and TK. Two or even three of these non-essential genes may thus be inactivated.

In particular, to reduce toxicity in vivo, we have inserted an inactivating mutation in the non-essential gene VMW65 of an HSV of the invention to reduce immediate-early (IE) gene expression, and thus also the level of expression of the genes regulated by these proteins. Furthermore, we have also produced herpes simplex viruses with deletions in the gene encoding the virion host shut-off protein (vhs). Vhs is a protein carried in the virion and is responsible for destabilising mRNA and thus reducing host protein synthesis in favour of translation from the more rapidly produced viral RNA which accompanies infection with a wild type virus.

Consequently, in a preferred embodiment of the present invention, the HSV of the invention also lacks a functional vhs gene and/or a functional VMW65 gene (due to a mutation in said VMW65 gene which abolishes its transcriptional-activation activity). A particularly preferred virus of the invention lacks a functional ICP4 gene, a functional ICP34.5 gene, a functional vhs gene and a functional VMW65 gene due to a mutation in said VMW65 gene which abolishes its transcriptional-activation activity.

The herpes simplex viruses of the invention can be used, for example, for delivering therapeutic genes in methods of treatment of diseases of, or injuries to, the nervous system, including Parkinson's disease, spinal injury or strokes, or diseases of the eye, heart or skeletal muscles, or malignancies. The present invention also relates to methods for studying the function of genes in mammalian cells, for example in identifying genes complementing cellular dysfunctions, or studying the effect of expressing mutant genes in wild-type or mutant mammalian cells. The methods of the present invention may be used in particular for the functional study of genes implicated in disease.

The invention further provides an HSV of the invention which carries a heterologous gene. The term heterologous gene is intended to embrace any gene not found in the HSV genome. The heterologous gene may be any allelic variant of a wildtype gene, or it may be a mutant gene. Heterologous genes are preferably operably linked to a control sequence permitting expression of said heterologous gene in mammalian cells, preferably cells of the central or peripheral nervous system, or cells of the eye, heart or skeletal muscle, more preferably cells of the central or peripheral nervous system. The HSV of the invention may thus be used to deliver a heterologous gene to a mammalian cell where it will be expressed. Such vectors are useful in a variety of applications, for example, in gene therapy, or in vitro assay methods or for the study of HSV gene regulation.

The heterologous gene preferably encodes a polypeptide of therapeutic use, including polypeptides that are cytotoxic or capable of converting a precursor prodrug into a cytotoxic compound.

The invention further provides herpes simplex viruses of the invention, carrying a heterologous gene, for use in the treatment of humans and animals. For example, such viruses may be used in the treatment of diseases of, or injury to, the nervous system, including Parkinson's disease, spinal injury or strokes or disease of the eye, heart or skeletal muscle, or malignancies.

The HSV of the present invention may also be used in methods for studying the function of genes in mammalian cells, for example in identifying genes complementing cellular dysfunctions, or studying the effect of expressing mutant genes in wild-type or mutant mammalian cells. The methods of the present invention may be used in particular for the functional study of genes implicated in disease.

The invention also provides a method for producing a herpes simplex virus of the present invention, said method comprising modifying the ICP34.5 and ICP4 genes (and optionally the VMW65 and/or vhs genes) of a herpes simplex virus so as to inactivate said genes functionally, provided that the ICP27 gene remains intact and/or functional.

DETAILED DESCRIPTION OF THE INVENTION

A. Viral Strains

The herpes simplex viruses of the invention may be derived from, for example, HSV1 or HSV2 strains, or derivatives thereof, preferably HSV1. Derivatives include inter-type recombinants containing DNA from HSV1 and HSV2 strains. Derivatives preferably have at least 70% sequence homology to either the HSV1 or HSV2 genomes, more preferably at least 80%, even more preferably at least 90 or 95%. Other derivatives which may be used to obtain the viruses of the present invention include strains that already have mutations in either ICP4, ICP34.5, VMW65 or vhs, for example strain 1716 (MacLean et al., 1991), strains R3616 and R4009 (Chou and Roizman, 1992) and R930 (Chou et al., 1994) all of which have mutations in ICP34.5, strain d120 which has a deletion in ICP4 (DeLuca et al., 1985). Use of these strains will reduce the number of steps required to produce the mutant HSV strains of the present invention.

The terminology used in describing the various HSV genes is as found in Coffin and Latchman, 1996.

B. Complementing Cell Lines

The virus of the invention is propagated on a cell line expressing ICP4, for example E5 cells (DeLuca et al., 1985) or B4 cells (see Example 1), preferably B4 cells.

ICP4-expressing cell lines can be produced by co-transfecting mammalian cells, for example the Vero or BHK cells, with a vector, preferably a plasmid vector, comprising a functional HSV ICP4 gene capable of being expressed in said cells, and a vector, preferably a plasmid vector, encoding a selectable marker, for example neomycin resistance. Clones possessing the selectable marker are then screened further to determine which clones also express functional ICP4, for example on the basis of their ability to support the growth of ICP4$^-$ HSV strains, using methods known to those skilled in the art.

Cell lines which do not allow reversion of an ICP4$^-$ mutant HSV strain to a strain with functional ICP4 are produced as described above, ensuring that the vector comprising a functional ICP4 gene does not contain sequences that overlap with (i.e. are homologous to) sequences remaining in the ICP4$^-$ mutant virus.

C. Methods of Mutation

The ICP4, ICP34.5, vhs and other HSV genes may be rendered functionally inactive by several techniques well known in the art. For example, they may be rendered functionally inactive by deletions, substitutions or insertions, preferably by deletion. Deletions may remove portions of the genes or the entire gene. For example, deletion of only one nucleotide may be made, resulting in a frame shift. However, preferably larger deletions are made, for example at least 25%, more preferably at least 50% of the total coding and non-coding sequence (or alternatively, in absolute terms, at least 10 nucleotides, more preferably at least 100 nucleotides, most preferably, at least 1000 nucleotides). It is particularly preferred to remove the entire gene and some of the flanking sequences. Inserted sequences may include the heterologous genes described below. In particular, it is preferred to insert the heterologous gene into ICP4. In the case of the VMW65 gene, the entire gene is not deleted since it encodes an essential structural protein, but a small inactivating insertion is made which abolishes the ability of VMW65 to activate transcriptionally IE genes (e.g. as in Ace et al., 1989, Smiley and Duncan, 1997, or other mutations resulting in a similar effect).

Mutations are made in the herpes simplex viruses by homologous recombination methods well known to those skilled in the art, or alternatively by direct ligation into linearised HSV genomic DNA or by any other means which may be known or developed by those skilled in the art. For example, HSV genomic DNA is transfected together with a vector, preferably a plasmid vector, comprising the mutated sequence flanked by homologous HSV sequences. The mutated sequence may comprise deletions, insertions or substitutions, all of which may be constructed by routine techniques. Insertions may include selectable marker genes, for example lacZ, for screening recombinant viruses by, for example, β-galactosidase activity.

D. Heterologous Genes and Promoters

The mutant HSV strains of the invention may be modified to carry a heterologous gene, that is to say a gene other than one present in the HSV genome. The term "heterologous gene" comprises any gene other than one present in the HSV genome. The heterologous gene may be any allelic variant of a wild-type gene, or it may be a mutant gene. The term "gene" is intended to cover nucleic acid sequences which are capable of being at least transcribed. Thus, sequences encoding mRNA, tRNA and rRNA are included within this definition. Nucleic acids may be, for example, ribonucleic acid (RNA) or deoxyribonucleic acid (DNA) or analogues thereof. The sequences may be in the sense or antisense orientation with respect to the promoter. Antisense constructs can be used to inhibit the expression of a gene in a cell according to well-known techniques. Sequences encoding mRNA will optionally include some or all of 5' and/or 3' transcribed but untranslated flanking sequences naturally, or otherwise, associated with the translated coding sequence. It may optionally further include the associated transcriptional control sequences normally associated with the transcribed sequences, for example transcriptional stop signals, polyadenylation sites and downstream enhancer elements.

The heterologous gene may be inserted into the HSV genome by homologous recombination of HSV strains with, for example, plasmid vectors carrying the heterologous gene flanked by HSV sequences. The heterologous gene may be introduced into a suitable plasmid vector comprising HSV sequences using cloning techniques well known in the art. The heterologous gene may be inserted into the HSV genome at any location provided that the virus can still be propagated. It is preferred that the heterologous gene is inserted into the essential gene ICP4.

The transcribed sequence of the heterologous gene is preferably operably linked to a control sequence permitting expression of the heterologous gene in mammalian cells, preferably cells of the central and peripheral nervous system. The term "operably linked" refers to a juxtaposition wherein the components described are in a relationship permitting them to function in their intended manner. A control sequence "operably linked" to a coding sequence is ligated in such a way that expression of the coding sequence is achieved under conditions compatible with the control sequence.

The control sequence comprises a promoter allowing expression of the heterologous gene and a signal for termination of transcription. The promoter is selected from promoters which are functional in mammalian, preferably human, cells. The promoter may be derived from promoter sequences of eukaryotic genes. For example, it may be a promoter derived from the genome of a cell in which expression of the heterologous gene is to occur, preferably a cell of the mammalian central or peripheral nervous system. With respect to eukaryotic promoters, they may be promoters that function in a ubiquitous manner (such as promoters of β-actin, tubulin) or, alternatively, a tissue-specific manner (such as promoters of the genes for pyruvate kinase). They may also be promoters that respond to specific stimuli, for example promoters that bind steroid hormone receptors. Viral promoters may also be used, for example the Moloney murine leukaemia virus long terminal repeat (MMLV LTR) promoter or promoters of HSV genes.

The HSV LAT promoter, and promoters containing elements of the LAT promoter region, may be especially preferred because there is the possibility of achieving long-term expression of heterologous genes during latency. In particular, an expression cassette consisting essentially of a LAT P2 region,which does not itself here act as a promoter, linked to a promoter and a heterologous gene in that order is especially preferred (WO 98/30707).

The term "long-term expression" is taken to mean expression of a heterologous gene in a cell infected with a herpes simplex virus of the invention even after the herpes simplex virus has entered latency. Preferably, this is for at least two weeks, more preferably at least one or two months after infection, even more preferably for the lifetime of the cell.

The expression cassette may further comprise a second promoter and a second heterologous gene operably linked in that order to said HSV LAT P2 region and in the opposite orientation to the first promoter and first heterologous gene wherein said second promoter and second heterologous gene are the same as or different to the first promoter and first heterologous gene. Thus a pair of promoter/heterologous gene constructs in opposite orientations flank a single LAT P2 region allowing the long term expression of pairs of heterologous genes, which may be the same or different, driven by the same or different promoters. Furthermore, the product of the first heterologous gene may regulate the expression of the second heterologous gene (or vice-versa) under suitable physiological conditions.

The expression cassette can be constructed using routine cloning techniques known to persons skilled in the art (see, for example, Sambrook et al., 1989, Molecular Cloning—a laboratory manual; Cold Spring Harbor Press). Furthermore, the construction of particular HSV strains comprising such an expression cassette is described in the Examples.

The LAT P2 region is here defined as HSV1 nucleotides 118866–120219 (GenBank HE1CG: from PstI-BstXI sites) in HSV1 strain 17+, fragments or derivatives of this region, including homologous regions of HSV2 strains and other strains of HSV1, which are capable of providing a long-term expression capability to promoters to which they are linked.

It may also be advantageous for the promoters to be inducible so that the levels of expression of the heterologous gene can be regulated during the life-time of the cell. Inducible means that the levels of expression obtained using the promoter can be regulated. For example, in a preferred embodiment where more than one heterologous gene is inserted into the HSV genome, either both at the same site in the HSV genome or at different sites, one inserted promoter would comprise a promoter responsive to the tet repressor/VP16 transcriptional activator fusion protein previously reported (Gossen and Bujard, 1992, Gossen et al, 1995), and driving the heterologous gene the expression of which is to be regulated. The second inserted promoter would comprise a strong promoter (e.g. the CMV IE promoter) driving the expression of the tet repressor/VP16 fusion protein. Thus in this example expression of the first heterologous gene would depend on the presence or absence of tetracycline. More than one promoter/heterologous gene the expression level of which is to be regulated cassette may be inserted into the HSV genome in embodiments of the current invention allowing the level of expression of multiple genes to be regulated for example by the administration of tetracycline or other substance capable of regulating expression levels from the regulable promoter(s) in use.

In addition, any of these promoters may be modified by the addition of further regulatory sequences, for example enhancer sequences (including elements of the LAT region). Chimeric promoters may also be used comprising sequence elements from two or more different promoters described above, for example an MMLV LTR/LAT fusion promoter (Lokensgard et al, 1994) or promoters comprising elements of the LAT region (see above).

The heterologous gene may encode, for example, proteins involved in the regulation of cell division, for example mitogenic growth factors including neurotrophic growth factors (such as brain-derived neurotrophic factor, glial cell derived neurotrophic factor, NGF, NT3, NT4 and NT5, GAP43), cytokines (such as α-, β- or γ-interferon, interleukins including IL-1, IL-2, tumour necrosis factor, or insulin-like growth factors I or II), protein kinases (such as MAP kinase), protein phosphatases and cellular receptors for any of the above. The heterologous gene may also encode enzymes involved in cellular metabolic pathways, for example enzymes involved in amino acid biosynthesis or degradation (such as tyrosine hydroxylase), purine or pyrimidine biosynthesis or degradation, and the biosynthesis or degradation of neurotransmitters, such as doparnine, or protein involved in the regulation of such pathways, for example protein kinases and phosphatases. The heterologous gene may also encode transcription factors or proteins involved in their regulation, for example members of the Brn3 family (including Brn3a, Brn3b and Brn3c) or pocket proteins of the Rb family such as Rb or p107, membrane proteins (such as rhodopsin), structural proteins (such as dystrophin) or heat shock proteins such as hsp27, hsp65, hsp70 and hsp90.

Preferably, the heterologous gene encodes a polypeptide of therapeutic use, or whose function or lack of function may be important in a disease process. For example, of the proteins described above, tyrosine hydroxylase can be used in the treatment of Parkinson's disease, rhodopsin can be used in the treatment of eye disorders, dystrophin may be used to treat muscular dystrophy, and heat shock proteins can be used to treat disorders of the heart and brain associated with ischaemic stress. Polypeptides of therapeutic use may also include cytotoxic polypeptides such as ricin, or enzymes capable of converting a precursor prodrug into a cytotoxic compound for use in, for example, methods of virus-directed enzyme prodrug therapy or gene-directed enzyme prodrug therapy. In the latter case, it may be desirable to ensure that the enzyme has a suitable signal sequence for directing it to the cell surface, preferably a signal sequence that allows the enzyme to be exposed on the exterior of the cell surface whilst remaining anchored to cell membrane. Suitable enzymes include bacterial nitroreductase such as *E. coli* nitroreductase as disclosed in WO93/08288 or carboxypeptidase, especially carboxypeptidase CPG2 as disclosed in WO88/07378. Other enzymes may be found by reference to EP-A-415731. Suitable prodrugs include nitrogen mustard prodrugs and other compounds such as those described in WO88/07378, WO89/10140, WO90/02729 and WO93/08288 which are incorporated herein by reference.

Heterologous genes may also encode antigenic polypeptides for use as vaccines. Preferably such antigenic polypeptides are derived from pathogenic organisms, for example bacteria or viruses, or from tumours.

Heterologous genes may also include marker genes (for example encoding β-galactosidase or green fluorescent protein) or genes whose products regulate the expression of other genes (for example, transcriptional regulatory factors including the tet repressor/VP16 transcriptional activator fusion protein described above).

Gene therapy and other therapeutic applications may well require the administration of multiple genes. The expression of multiple genes may be advantageous for the treatment of a variety of conditions—e.g. using multiple neurotrophic factors. HSV is uniquely appropriate as it does not have the limited packaging capabilities of other viral vector systems. Thus multiple heterologous genes can be accommodated within its genome. There are, for example, at least two ways in which this could be achieved. For example, more than one heterologous gene and associated control sequences could be introduced into a particular HSV strain. It would also be possible to use pairs of promoters (the same or different promoters) facing in opposite orientations away from a centrally located LAT P2 element, these promoters each driving the expression of a heterologous gene (the same or different heterologous gene) as described above. Alternatively heterologous genes may be inserted at multiple sites within the HSV genome.

E. Administration

The mutant herpes simplex viruses of the present invention may thus be used to deliver therapeutic genes to a human or animal in need of treatment. Delivery of therapeutic genes using the mutant herpes simplex viruses of the invention may be used to treat for example, Parkinson's disease, disorders of the nervous system, spinal injury, strokes or malignancies, for example gliomas.

One method for administered gene therapy involves inserting the therapeutic gene into the genome of the mutant herpes simplex virus of the invention, as described above, and then combining the resultant recombinant virus with a pharmaceutically acceptable carrier or diluent to produce a pharmaceutical composition. Suitable carriers and diluents include isotonic saline solutions, for example phosphate-buffered saline. The composition may be formulated for parenteral, intramuscular, intravenous, subcutaneous, intraocular or transdermal administration.

The pharmaceutical composition is administered in such a way that the mutated virus containing the therapeutic gene for gene therapy, can be incorporated into cells at an appropriate area. For example, when the target of gene therapy is the central or peripheral nervous system, the composition could be administered in an area where synaptic terminals are located. The pharmaceutical composition is typically administered to the brain by stereotaxic inoculation. When the pharmaceutical composition is administered to the eye, sub-retinal injection is typically the technique used.

The amount of virus administered is in the range of from $10^4$ to $10^{10}$ pfu, preferably from $10^5$ to $10^8$ pfu, more preferably about $10^6$ to $10^7$ pfu. When injected, typically 1 to 10 $\mu$l of virus in a pharmaceutically acceptable suitable carrier or diluent is administered.

The routes of administration and dosages described are intended only as a guide since a skilled practitioner will be able to determine readily the optimum route of administration and dosage for any particular patient and condition.

F. Assay Methodologies

The mutant herpes simplex viruses of the invention can also be used in methods of scientific research. Thus, a further aspect of the present invention relates to methods of assaying gene function in mammalian cells, either in vitro or in vivo. The function of a heterologous gene could be determined by a method comprising:

(a) introducing said heterologous gene into a mutant herpes simplex virus of the invention;

(b) introducing the resulting virus into a mammalian cell line; and (c) determining the effect of expression of said heterologous gene in said mammalian cell-line.

For example, the cell-line may have a temperature-sensitive defect in cell division. When an HSV strain comprising a heterologous gene according to the invention is introduced into the defective cell-line and the cell-line grown at the restrictive temperature, a skilled person will easily be able to determine whether the heterologous gene can complement the defect in cell division. Similarly, other known techniques can be applied to determine if expression of the heterologous gene can correct an observable mutant phenotype in the mammalian cell-line.

This procedure can also be used to carry out systematic mutagenesis of a heterologous gene to ascertain which regions of the protein encoded by the gene are involved in restoring the mutant phenotype.

This method can also be used in animals, for example mice, carrying so-called "gene knock-outs". A wild-type heterologous gene can be introduced into the animal using a mutant HSV strain of the invention and the effect on the animal determined using various behavioural, histochemical or biochemical assays known in the art. Alternatively, a mutant heterologous gene can be introduced into either a wild-type or "gene knock-out" animal to determine if disease-associated pathology is induced. An example of this is the use of genes encoding prions to induce Creutzfeld-Jacob and other prion-type diseases in the central nervous system of rodents. Other disease models may include those for Alzheimer's disease, motor neurone disease or Parkinson's disease.

Since it is possible to introduce at least two different heterologous genes into a cell due to the large capacity of the HSV genome, it will also be possible to study the interaction between two or more gene products.

Thus, the methods of the present invention may be used in particular for the functional study of genes implicated in disease.

The invention will be described with reference to the following Examples, which are intended to be illustrative only and not limiting.

EXAMPLES

Example 1

Production of Mutant Viruses

Viruses

ICP34.5 deletion mutants with a mutation producing a functional inactivation of the transcriptional-activating activity of VMW65 were produced by co-cultivation (in BHK cells with 3 mM HMBA) of strain 1716, containing a deletion in both copies of ICP34.5 (MacLean et al., 1991), with strain in1814 (Ace et al., 1989) containing a functionally inactivated VMW65 gene. The genomic structure of resultant plaques was analysed by methods known to those skilled in the art (restriction digestion of purified genomic DNA and Southern blotting) and virus containing both the in1814 and 1716 mutations further plaque-purified five times, giving the virus strain 1764. Growth of viruses containing the in1814 mutation or other mutations affecting the trans-activating activity of VMW65 (e.g. as in Smiley and Duncan, 1997) can be enhanced by inclusion of hexamethylene bisacetamide in the media used during virus growth (McFarlene et al, 1992).

Vhs/ICP34.5/VMW65 deletion mutants were produced by homologous recombination of plasmid pR15 with HSV strain 1764 DNA to generate virus 1764/pR15 deleted for ICP34.5, VMW65 and vhs and having a lacZ gene driven by the moloney murine leukaemia virus long terminal repeat (MMLV LTR) promoter (Shinnick et al., 1981) inserted into the coding region of vhs. Plasmid pR15 was constructed by insertion of an MMLVLTR/lacZ/pA cassette into the unique NruI site in the vhs gene. Thus restriction fragment KpnI-i from the HSV1 strain 17+ genome cloned into the PstI site of plasmid pAT153 (Northumbria Biologicals Ltd).

Both copies of ICP4 were removed from strain 1716 and strain 1764/pR15. This was achieved by homologous recombination of purified strain 1716 or strain 1764/pR15 genomic DNA with plasmid pΔ4/GFP. pΔ4/GFP was constructed using ICP4 flanking sequences (nts 123,459–126,774 [Sau3aI-Sau3aI] and nts 131,730–134,792 [SphI-KpnI] separated by XbaI and SalI sites derived from pSP72 [Promega], in which the construct was made). An approximately 0.8 kb NotI fragment (nts 124,945–125,723) containing the coding region for ICP34.5 was also removed to prevent the repair of the ICP34.5 deletion during homologous recombination with strain 1716 or strain 1764/pR15. A CMV/GFP/pA cassette was then inserted at the unique XbaI site giving pΔ4/GFP. The CMV gene was first excised from pEGFPN1 (Clontech) with AgeI and NotI and inserted between the EcoRI and NotI sites of pcDNA3 (Invitrogen) giving pcDNA3GFP. The CMV/GFP/pA cassette could then be excised from pcDNA3GFP for insertion into ICP4 flanking regions with NruI and BbsI. pΔ4/GFP was then introduced into strain 1716 and strain 1764/pR15 by homologous recombination as before and GFP expressing plaques identified by fluorescence microscopy and plaque purification on B4 cells (described below), giving virus strain 1716/Δ4 and virus strain 1764/pR15Δ4. Plaque purified virus could not give a productive infection on BHK cells not expressing ICP4.

Virus strain 17⁺/Δ4 was prepared as above except using strain 17+ genomic DNA and a plasmid containing ICP4 flanking regions from which the ICP34.5 gene had not been deleted by removal of the NotI fragment.

Nucleotide numbers refer to the HSV1 strain 17+ sequence (Genbank no. HE1CG).

Growth of Mutant HSV Strains Using Complementing Cell Lines

A complementing cell line (B4) allowing growth of ICP4 deleted viruses was generated by co-transfection of plasmid pICP4 DNA with neomycin resistance-encoding plasmid pMamNeo (Invitrogen) into BHK cells and the selection of neomycin resistant clones. Plasmid pICP4 was contains a DdeI-SphI fragment from the HSV1 genome [nts 126, 764–131,730], containing the ICP4 coding region and promoter, cloned between the EcoRV and SphI sites of pSP72 (Promega)

A clone highly permissive for the growth of an HSV1 ICP4 deletion mutant (B4) was selected for virus growth.

Example 2

Infection of Non-neuronal Cells in vitro Using HSV1 Strains of the Invention

HSV strains of the invention were tested on vero cells at high multiplicity of infection (MOI) for persistence in cell cultures using methods similar to Samaniego et al., 1998. Persistence of virus genomes from which gene expression can be re-stimulated provides an indication of the degree of cytotoxicity of the viruses to the cells. Here vero cells were infected in 24 well plates at an MOI of 20 with each of the strains 1764/pR15Δ4, 1716/Δ4 and 17⁺/Δ4. The cells were then incubated at 34° C./5% CO2 for the remainder of the experiment. GFP fluorescence was observed over time and at various times (2 days, 1 week, 2 weeks and 1 month) cell cultures were superinfected at an MOI of 20 with HSV strain zΔMN+ (which contains a lacZ insertion into the ICP27 gene; Howard et al., 1998).

These experiments showed that after 2 days with each of the viruses, strong fluorescence could be observed in >95% of the cells in each of the cultures, although signs of cytotoxicity were evident in cultures infected with, 1716/Δ4 and 17⁺/Δ4 (some loss of normal cell morphology could be observed). Cells infected with 1764/pR15Δ4 showed cell morphology identical to uninfected control cells, indicating reduced toxicity of this virus, although a transient reduction in the rate of cell division could be observed.

At 1 week after infection and at later time points up to one month non-superinfected cells showed dimishing GFP fluorescence in each case. However, while at one week this fluorescence could be re-stimulated by infection with virus zΔMN+ to some extent in all cases, at the 2 week and 1 month time points GFP fluorescence could only be significantly restimulated in cells originally infected with 1764/pR15Δ4, again demonstrating the reduced toxicity of this virus.

Example 3

Infection of Primary Neuronal Cells in vitro Using HSV1 Strains of the Invention The HSV strains of the invention were tested for toxicity in vitro using primary cultures of enteric neurons (derived from 7 day old Sprague-Dawley rat guts—Saffrey et al., 1991). These cultures showed considerably enhanced survival (as assessed by trypan blue staining) and maintenance of neuronal morphology after 3 days in culture after treatment in a 96 well microtitre dish with $2 \times 10^6$ pfu/well of 1764/pR15Δ4 as compared to 1716, 1764, 17+/Δ4 or 1764/pR15. Thus 80% of cells maintained neuronal processes after 3 days with 1764/pR15Δ4 as compared to approximately 20% with 1764/pR15 and 35% with 17+/Δ4.

Greater than 90% of surviving cells showed marker gene activity (lacZ and/or GFP depending on the virus used) using 1764/pR15Δ4, 17+/Δ4 or 1764/pR15, showing effective gene transfer using the virus vectors in vitro. The considerably reduced toxicity of 1764/pR15Δ4 as compared to the other viruses used is likely to be advantageous when the virus is used as a vector in vivo, particularly where long term gene expression is required.

Removal of ICP34.5 together with ICP4 provides a virus with considerably improved safety characteristics as compared to deletion of ICP4 alone. This is because the ICP34.5 gene does not need to be complimented for growth of the virus in culture, and thus the mutation can under no circumstances be repaired during virus growth. Thus even if ICP4 were repaired by recombination during virus growth, the resulting virus would still be deleted for ICP34.5, and would thus still be safe for use as a vector in vivo. Viruses deleted for ICP34.5 alone are non-neurovirulent when injected into the brains of test animals in vivo (see Chou et al., 1990). Further inactivating mutations in VMW65 and vhs reduces toxicity further.

Example 4

Gene Delivery in Vivo

Strains 1764/pR15Δ4, 1716/Δ4 and 17+/Δ4 were assessed for gene delivery efficiency in vivo following steriotaxic inoculation of the striatum of Sprague-Dawley rats using 5 microlitres of a 5×10exp7 pfu/ml stock of each virus inoculated over a period of 10 minuteus using an UltraMicroPump (World Precision Instruments) connected to a Hamilton Syringe and using a MicroFil needle (World Precision Instruments) for injection. Pairs of rats were killed at two days, 2 weeks and one month after inoculation and gene delivery assessed following fixation by perfusion in 2% paraformaldehyde in phosphate buffer, sectioning and examination for GFP expression by fluorescence microscopy.

High level GFP expression could be seen in large numbers of cells around the site of inoculation with all the viruses after two days. Thus initial gene delivery efficiencies are comparable between viruses deleted for only ICP4 and deleted for ICP4 and ICP34.5. Deletion of ICP34.5 thus does not reduce the efficiency of ICP4 deleted viruses as vectors even though such viruses have the advantage of improved safety over viruses deleted for ICP4 alone. However after two weeks only relatively small numbers of GFP +ve cells could be observed in animals inoculated with 1716/Δ4 and 17+/Δ4, considerably larger numbers of GFP +ve cells being observed with 1764/pR15Δ4 further demonstrating the reduced toxicity of this virus. At one month no GFP +ve cells could be observed with 1716/Δ4 and 17+/Δ4, some GFP +ve cells remaining with 1764/pR15Δ4 (GFP here being driven by the CMV IE promoter) again further demonstrating this point. When stained with X-gal, brain slices derived from 1764/pR15Δ4 inoculated animals at one month showed considerably more blue staining cells (indicating lacZ activity) than GFP +ve cells, probably reflecting the activity of the promoter here used to drive lacZ which is very similar to a promoter which has previously been shown to give gene expression in vivo during HSV latency (Lokensgard et al., 1994).

References

Coffin R S, Latchman D S. Herpes simplex virus-based vectors. In: Latchman D S (ed).
Genetic manipulation of the nervous system. Academic Press: London, 1996, pp 99–114.
MacLean A R et al. Herpes simplex virus type I deletion variants 1714 and 1716 pinpoint neurovirulence related sequences in Glasgow strain 17+ between immediate early gene I and the 'a' sequence. J Gen Virol 1991; 72: 632–639.
Shinnick T M et al. Nucleotide sequence of Moloney murine leukaemia virus. Nature 1981; 293: 543–548.
Morgenstern J P and Land H. A series of mammalian expression vectors and characterisation of their expression of a reporter gene in stably and transiently transfected cells. NAR 1990.; 18: 1068.
Ace C et al. Construction and characterisation of a herpes simplex virus type I mutant unable to transinduce immediate early gene expression. J Virol 1989; 63: 2260–2269.
McFarlane M, Daksis J I, Preston C M. Hexamethylene bisacetamide stimulates herpes-simplex virus immediate early gene-expression in the absence of trans-induction by VMW65. J Gen Virol 1992; 73: 285–292.
Reef Hardy, W and Sandri-Goldin R M. Herpes simplex virus inhibits host cell splicing and regulatory protein ICP27 is required for this effect J. Virol 1994; 68: 7790–7799.
Dobson, A T et al. A latent, non-pathogenic HSV1-derived vector stably expresses β-galactosidase in mouse neurons. Neuron 1990; 5: 353–360.
Chou, J., Kem, E R, Whitley, R J and Roizman, B. Mapping of herpes simplex virus-1 neurovirulence to ($_1$34.5, a gene nonessential for growth in culture. Science 1990; 250: 1262–1266.
Chiocca, A E et al. Transfer and expression of the lacZ gene in rat brain neurons by herpes simplex virus mutants. New Biol. 1990; 2: 739–736.
Chou, J. and Roizman, B. The ($_{\gamma 1}$34.5 gene of herpes simplex virus 1 precludes neuroblastoma cells from triggering total shutoff of protein synthesis characteristic of programmed cell death in neuronal cells. PNAS 1992; 89: 3266–3270.
Chou, J., Poon, A P W, Johnson, J. and Roizman B. Differential response of human cells to deletions and stop codons in the ($_1$34.5 gene of herpes simplex virus. J. Virol. 1994; 68: 8304–8311.

DeLuca N A et al. J. Virol. 1985; 56: 558–570.
Lokensgard J R et al. J. Virol. 1994; 68: 7148–7158.
Saffrey et al., Cell and Tissue Culture Research. 1991; 265: 527–534.
Smiley J R and Duncan J, J. Virol. 1997; 71: 6191–6193.
Howard M K et al. Gene Therapy 1998; 5: 1137–1147.
Samaniego L A et al. J. Virol. 1998; 72: 3307–3320.

What is claimed is:

1. A herpes simplex virus having a functional ICP27 gene and which lacks functional ICP4 and functional ICP34.5 genes, a functional vhs gene and a functional VMW65 gene due to a mutation in said VMW65 gene which abolishes its transcriptional-activation activity.

2. A virus according to claim 1 which is selected from the group consisting of an HSV1 strain, an HSV2 strains and an intertype recombinant containing DNA from an HSV1 strain and an HSV2 strain.

3. A virus according to claim 2 which is an HSV1 strain.

4. A virus according to claim 1 which carries at least one heterologous gene.

5. A virus according to claim 4 wherein said heterologous gene is operably linked to a control sequence permitting expression of said heterologous gene in mammalian cells.

6. A virus according to claim 5 wherein said mammalian cell is a cell of the central or peripheral nervous system of a mammal.

7. A virus according to claim 5 wherein said mammalian cell is a cell of the eye, heart or skeletal muscle of a mammal.

8. A virus according to claim 5 wherein said gene encodes a polypeptide which is cytotoxic.

9. A virus according to claim 5 wherein said gene encodes a polypeptide which converts a precursor prodrug into a cytotoxic compound.

10. A virus according to claim 5 wherein the heterologous gene is selected from the group consisting of genes encoding proteins involved in the regulation of cell division, enzymes involves in metabolic pathways, transcription factors, and heat shock proteins.

11. A composition comprising an HSV strain according to claim 5 together with a carrier or diluent.

12. A method for studying the function of a heterologous gene in a mammalian cell, which method comprises:

(a) introducing said heterologous gene into a herpes simplex virus according to claim 1;

(b) introducing the resulting herpes simplex virus into said mammalian cell such that said heterologous gene is expressed in said cell; and (c) determining the effect on said cell of expression of said heterologous gene in said mammalian cell to determine the function of said heterologous gene.

13. A method according to claim 12, wherein said heterologous gene is a gene implicated in causing disease.

14. A method according to claim 12 wherein said mammalian cell is dysfunctional in a particular cellular function, said heterologous gene is wild-type and the effect of expression of said heterologous gene is determined by an assay for said cellular function, to determine whether said gene restores said function to said mammalian cell.

15. A method according to claim 12 wherein said mammalian cell has one or more endogenous genes inactivated by mutation.

* * * * *

UNITED STATES PATENT AND TRADEMARK OFFICE
CERTIFICATE OF CORRECTION

PATENT NO. : 6,719,982 B1
DATED : April 13, 2004
INVENTOR(S) : Coffin et al.

It is certified that error appears in the above-identified patent and that said Letters Patent is hereby corrected as shown below:

Title page,
Item [56], References Cited, OTHER PUBLICATIONS, insert:
-- Panagiotidis C A et al: "Physical and functional interactions between herpes simplex virus immediate-early proteins ICP4 and ICP27." Journal of Virology, (02/1997) 71 (2) 1547-57.
Coffin R S et al: "Gene delivery to the central and peripheral nervous systems of mice using HSV1 ICP34.5 deletion mutant vectors." Gene Therapy, (10/1996) 3 (10) 886-92. --

Signed and Sealed this

Eighteenth Day of January, 2005

JON W. DUDAS
*Director of the United States Patent and Trademark Office*